Figure 1:
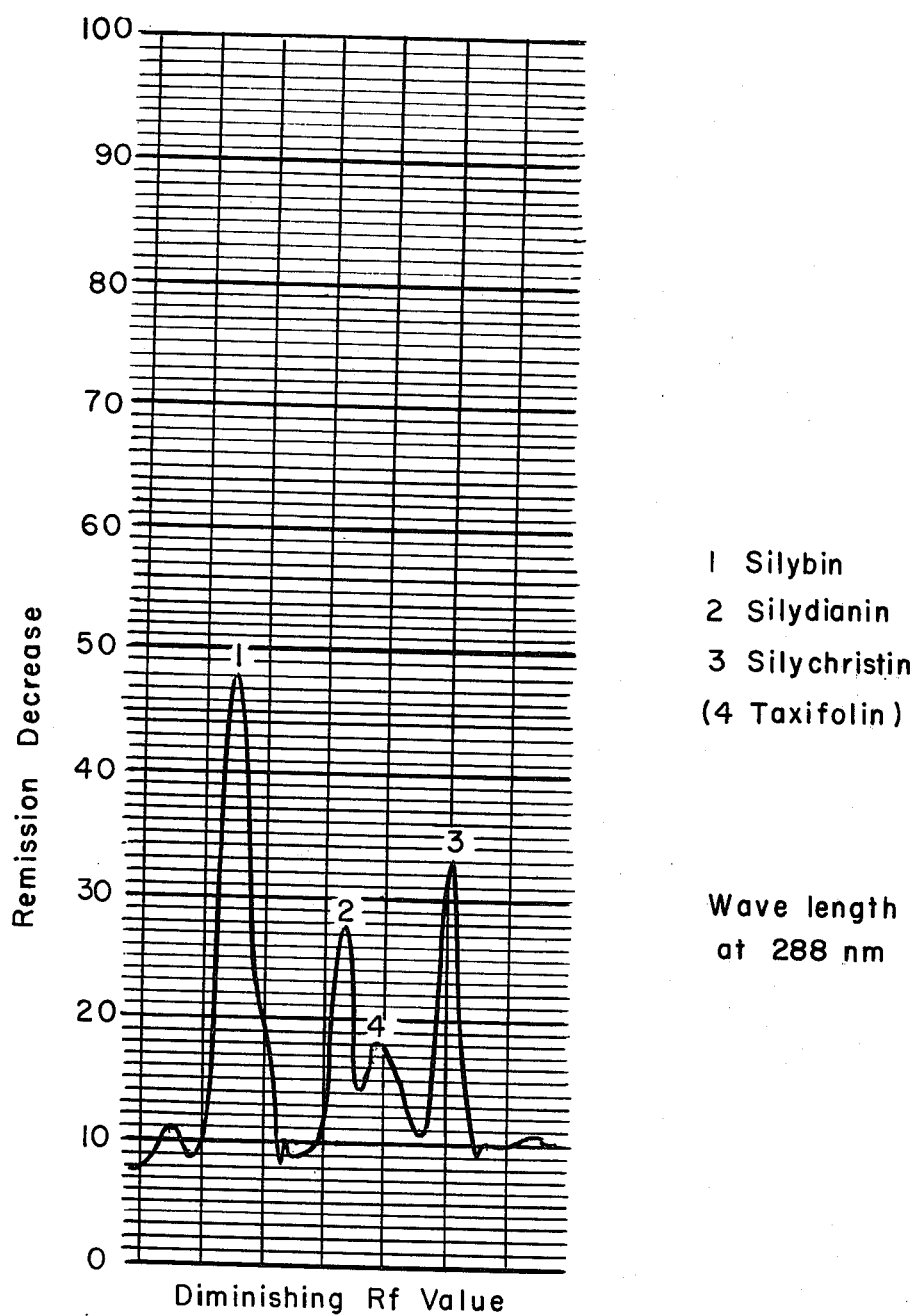

United States Patent [19]

Madaus et al.

[11] 4,368,195
[45] Jan. 11, 1983

[54] METHOD FOR THE EXTRACTION OF SILYMARIN FROM PLANTS

[75] Inventors: Rolf Madaus, Kön-Brück; Klaus Görler, Bensberg-Refrath; Werner Molls, Odenthal-Schmeisig, all of Fed. Rep. of Germany

[73] Assignee: Dr. Madaus & Co., Cologne, Fed. Rep. of Germany

[21] Appl. No.: 267,232

[22] Filed: May 26, 1981

Related U.S. Application Data

[63] Continuation of Ser. No. 191,722, Sep. 29, 1980, abandoned.

[30] Foreign Application Priority Data

Sep. 4, 1979 [DE] Fed. Rep. of Germany ....... 2914330

[51] Int. Cl.³ .............................................. A61K 35/78
[52] U.S. Cl. ................................................. 424/195
[58] Field of Search ........................................ 424/195

[56] References Cited

U.S. PATENT DOCUMENTS 3,773,932 11/1973 Madaus ............................... 424/195
3,864,484 2/1975 Madaus ............................... 424/195

Primary Examiner—Donald B. Moyer
Attorney, Agent, or Firm—Felfe & Lynch

[57] ABSTRACT

This invention is directed to an improved method for the extraction of silymarin (silymarin I–IV), in which a large part of the oil is removed from the fruits of Silybum marianum by cold pressing, the compressed mass is broken up, the pressed residue in extracted with ethyl acetate and the ethyl acetate extract is evaporated and processed.

4 Claims, 1 Drawing Figure

1 Silybin
2 Silydianin
3 Silychristin
(4 Taxifolin)

Wave length
at 288 nm

1 Silybin
2 Silydianin
3 Silychristin
(4 Taxifolin)

Wave length at 288 nm

METHOD FOR THE EXTRACTION OF SILYMARIN FROM PLANTS

This is a continuation of application Ser. No. 191,722, filed Sept. 29, 1980, now abandoned.

The invention concerns a method for the isolation of pure silymarin by extraction from the fruits of the milk thistle (Silybum marianum Gaertn.).

In technical usage the term silymarin is used to denote the silymarin group, i.e. the polyhydroxyphenylchromanones (silymarin I to silymarin IV) which can be isolated from the fruits of the milk thistle with 70-80% purity, depending on the quality of the crude drug. (Dt-AS No. 1 923 082).

Silymarin I, silymarin II and silymarin III are isomers having the empirical formula $C_{25}H_{22}O_{10}$. In the literature dealing with their structural formulae they have been given the names silybin, silydianin and silychristin. (Dt-AS No. 1 923 082; PELTER, A. and HÄNSEL, R., Tetrahedron Letters, London 25, 2911, 1968; WAGNER, H., HÖHAMMER, L., SELIGMANN, O., and FARNSWORTH, N. R., Tetrahedron Letters No. 31, pages 2675-2678; 1970; WAGNER, H., SELIGMANN, O., HÖRHAMMER, L. and SEITZ, M., Tetrahedron Letters No. 22, pages 1895-1899, 1971). Silymarin IV is taxifolin (Dt-AS No. 1 923 082).

Silymarin is a valuable agent for the therapy of liver diseases, and the silymarin mixture, by virtue of synergism has a greater effect than the sum of the effects of the separate isomers (Dt-AS No. 1 923 082).

A method for the isolation of silymarin (silymarin I-IV) is known from Dt-AS No. 1 923 082. In this method the dried seeds of Silybum marianum Gaertn. are mechanically pressed so as to rid them of the major part of the fatty oil. The pressed residue is then thoroughly extracted with ethyl acetate, the ethyl acetate solution is evaporated, the dry residue is redissolved in anhydrous methanol, the solution is defatted by repeated uniform countercurrent partition, and the fat-free methanolic solution is evaporated to dryness in vacuo. This gives a 70-80% polyhydroxphenylchromanone mixture (silymarin I-IV). The proportions of silymarin I, II and III are approximately 3:1:1. The amount of silymarin IV (taxifolin) is approximately 2-3% of the total silymarin content.

Dt-Os No. 2 020407 represents a further technical advance. The procedure set out in this OLS deals with the isolation of silymarin without preliminary defatting. It is based on direct overall extraction by a "solvent mixture of alcohol-water-a lower fatty acid ester or a chlorinated hydrocarbon" and separation of the fatty constituents "by subsequently distilling off 10-40% of the volume of the resulting extract solution, leaving it to stand and then removing the fats which rise to the surface of the solution". According to the claim, this method yields a 40% silymarin extract; the patent claim then goes on to recommend recrystallization from methanol, without giving any further information regarding appropriate technical measures. On attempting to carry out this procedure the claims proved not reproducible, and approximately 13% of the original fat was still present in the end product.

A further method is given in Dt-OS No. 2 017 789. The end products of this method are claimed to contain 40-70% of silymarin, and the yield of end product ranges from 0.3% to a maximum of 2.4% (of 40% silymarin).

A practical trial showed that this method, too, was not reproducible.

A further contribution is to be found in French Pat. No. 72.14042, which concerns the production of an extract from Silybum marianum without preliminary defatting. It is claimed that the end product contains approximately 82% of polyhydroxyphenylchromones; silymarins are stated to constitute 50% of this 82%. It may be noted that silymarin belongs to a different class of compounds, namely the polyhydroxyphenylchromanones and not the polyhydroxyphenylchromones. This method also is not reproducible.

It has so far proved impossible to make any substantial improvement on the method set out in Dt-AS No. 1 923 082. Difficulties arise primarily in separating the active constituents form the crude drug while preserving the mixture of silymarins present in it, and secondly in separating this mixture from approximately 30% of fatty oils and other incidental substances which are not easily removed. These difficulties have only been partially overcome by Dt-AS No. 1 923 082.

As it is a valuable agent for the treatment of liver disease, there is a demand for silymarin in the highest possible concentration—indeed in concentrations higher than those available in the present state of technical progress.

The purpose of the present invention is to devise a new process for the isolation of pure silymarin (silymarin I-IV) substantially free from incidental substances and containing all the natural isomers. This new process is intended to lead along a simple pathway to a higher yield of an outstandingly pure product. Surprisingly enough, it has proved possible to devise a process which avoids the disadvantages of the previous methods, which can be operated economically and which yields pure silymarin (silymarin I-IV) (purity 90-96%), measured according to the method of Wagner, Hörhammer, Seligmann and Farnsworth.

This invention concerns a method for isolating silymarin (silymarin I-IV) according to which the fruits of silybum marianum are freed from a large proportion of their fatty oil by cold pressing, the pressed mass is pulverized, the pressed residue extracted with ethyl acetate, and the ethyl acetate extract is evaporated and further processed. The features of the invention are as follows.

(a) the pressed residue is extracted several times with anhydrous ethyl acetate and the extract separated from the crude drug residue, (b) the residue left after evaporating the combined ethyl acetate extracts is defatted by repeated solid-liquid extraction with light petroleum or, (b') the residue remaining after evaporation is dissolved in methanol and the solution is defatted by repeated liquid-liquid extraction with light petroleum, (c) as much as possible of the defatted residue (b) is dissolved in methanol and the solution separated from the undissolved fraction or, (c') the defatted methanolic solution (b') is separated from the light petroleum.

(d) the methanolic solution is mixed with a chlorinated lower alkane as solvent together with water. The mixture is shaken, and the aqueous-methanolic solution is separated and retained, (e) the chlorinated solvent phase is extracted several times by stirring with methanol and water and decanted, (f) the combined aqueous-methanolic phases are evaporated, (g) the residue left on evaporation is suspended in a little methanol, the suspension is then stirred into water and after centrifuging the precipitate is washed several times with water, (h) the precipitate is dried in vacuo, pulverized and again dried in vacuo.

The main steps in the chosen procedure for carrying out the method which is the subject of this invention are as follows:

(a) the pressed residue is extracted from twice to four times, preferably three times, for ½ to 1½ hours, preferably 1 hour, with anhydrous ethyl acetate at 65°–76° C., preferably 75° C., in the proportions 1:8–1:12, preferably 1:10, with vigorous stirring and the extracted crude drug is removed, (b) the combined ethyl acetate extracts are evaporated at 40°–55° C., preferably 50° C., in vacuo at 15 mbar, (c) the residue left on evaporation is defatted by solid-liquid extraction with light petroleum 60°/70° in the proportions 1:15–1:25, preferably 1:20. This extraction is carried out three times for periods of 10–20 minutes, preferably 15 minutes.

(d) the defatted residue is dissolved in 6–10 times, preferably 8 times, its weight of methanol and the undissolved fraction is removed, (e) chloroform and water, each in volumes equal to that of the methanolic solution, are added to the latter and the mixture is vigorously stirred for 15 minutes and decanted, (f) the cloroform phase is mixed with methanol and water in proportions by volume 1:1:1 and stirred vigorously for 15 minutes. This process is carried out five times in all, the chloroform phase being removed at the end of each extraction, (g) the combined aqueous-methanolic phases are evaporated at 30°–50° C., preferably 40° C., in vacuo at 15 mbar, (h) the residue left on evaporation is suspended in methanol in the proportions 1:4–1:6, preferably 1:5, and the suspension is stirred into 8 to 12 times, preferably 10 times, its volume of water. The precipitate is separated by centrifugation and washed repeatedly with water, (i) the precipitate is dried for 20–30 hours, preferably 24 hours, at 30°–50° C., preferably 40° C., in vacuo at 10 mbar. It is then pulverized and the pulverized product is again dried at 30°–50° C., preferably 40° C., in vacuo at 10 mbar.

The products isolated in this way have a silymarin (silymarin I–IV) content of 90–96%, calculated in terms of the anhydrous substance.

As regards production technology, the individual steps and the specific procedures have been selected so as to ensure that the mixture of active substances present in the crude drug is almost completely recovered. Any deviation from these procedures would result in partial or total loss of one or other of the compounds. This difficulty assumes growing proportions as the concentration of the mixture of active substances rises, especially during the later stages of the method, because the active substances tend to be lost, either as individual compounds or as the mixture, with the incidental substances from which they have to be separated.

The method which is the subject of this invention has been devised with due attention to these points, so that it gives an optimal yield of a pure product containing the isomers in substantially the same proportion as in the crude drug.

It is a remarkable fact that only by a carefully chosen combination of production techniques, solvents or solvent systems and physical or chemical conditions the optimal product can be obtained.

By subjecting the fruits of Silybum marianum to cold pressing it is possible to prevent any chemical breakdown or polymerization of the silymarin and to avoid an intimate emulsification of the silymarin and the incidental substances in the fatty oil, an event which would hinder their subsequent separation. The crude drug is partially defatted by the pressing, approximately 25–30% of the oil being expelled.

The fine pulverization step speeds up the subsequent extraction, because it allows the solvent to penetrate more easily into the crude drug particles.

One crucial feature of this process is that anhydrous ethyl acetate is used for the ethyl acetate extraction. The maximum permissible water content is 0.5%. If the water content exceeds 0.5%, it will be impossible to separate the incidental substances during the subsequent steps in the procedure. This remarkable effect, taken in combination with the other rechnical procedures, is vital for the success of the process, namely the isolation of pure silymarin.

The ratio of crude drug to solvent during the ethyl acetate extraction is 1:8 to 1:12, preferably 1:10. This ratio has been selected so as to ensure that the silymarin is specifically and safely dissolved, without any unnecessary excess of solvent. By repeating the extraction twice to four times, preferably three times, complete removal of the silymarin from the crude drug is guaranteed. The working temperature of 60°–80° C., preferably 75° C., favours complete solution of the active substances while at the same time avoiding any degradation of the chemical compounds present in the drug.

Stirring with an intensive stirrer causes mechanical disintegrtion of the crude drug, a change which facilitates extraction. The short time of ½ to 1½ hours, preferably 1 hour, chosen for each of the extraction steps nevertheless ensures that extraction shall be complete.

The combined ethyl acetate extracts are evaporated at low temperature in vacuo in such a way as to avoid any risk of degrading the active substance.

The next step is repeated solid-liquid defatting of the residue with light petroleum using a relatively high proportion of residue to light petroleum, e.g. approx. 1:20. This has the advantage that the fatty oil can be completely remove in a short time and without elaborate apparatus—as compared for example with an elaborate liquid-liquid countercurrent extraction process in the present state of technical development.

Furthermore, the solid-liquid separation process avoids any loss of active substances, as often occurs during liquid-liquid extraction, because the solvent used for purification emulsifies or dissolves a proportion of the solvent containing the active substance.

Methanol, a relatively inexpensive solvent, is particularly suitable for redissolving the defatted residue by virtue of its powerful solvation properties. Silymarin (silymarin I–IV) is easily soluble in methanol. The high proportion of residue to solvent has been chosen to ensure that the silymarin (silymarin I–IV) shall be completely redissolved. No silymarin remains in the residue.

One new and particularly ingenious feature is the use of chlorinated organic solvents, in particular chlorine substituted lower alkanes such as chloroform, methylene chloride, 1,2-dichloroethane or trichlorethylene, preferably chloroform, for separating the remaining incidental substances from the silymarin (silymarin I–IV).

This ensures that the silymarin as a whole undergoes no loss and that none of the isomers escapes. This process gets rid of further lipophilic incidental substances which were not removed during the defatting step together with the oil and light petroleum, and also other less strongly polar incidental substances, which were at first dissolved in the methanol but which behave appropriately in a partition phase system. The solution equilibrium (phase diagram) of the selected solvent system—both in its nature and its quantity—in this case methanol-water-chloroform 1:1:1, is particularly suitable for silymarin (silymarin I–IV) and any incidental substances which may still be present, because good separation into two phases can be achieved with this solvent system. The dissociation zone of the phase diagram comprises the stated solvent proportions.

The partition coefficient of silymarin (silymarin I–IV) between the two phases is very high. After carrying out six extractions by shaking in a system consisting of methanol/chloroform/water 1/1/1 (v/v/v) the proportion of silymarin in the combined aqueous-methanol phases to that remaining in the chloroform phase is as 13:1.

In this way the silymarin (silymarin I–IV) can be almost completely extracted from the methanolic phase.

One remarkable result obtained by this invention is that silymarin I to IV remain in thier due proportions as individual compounds in the aqueous-methanolic phase, so that the ratio of the isomers is preserved.

The aqueous-methanolic phase is evaporated to dryness in vacuo at low temperature with due precautions to prevent decomposition and the residue is suspended in water for repeated washing. This washing process has proved advantageous in that it overcomes the difficulties caused by blocking of the filters by impurities in the product during ordinary filtration processes.

As opposed to the methods available in the present state of technical development, this invention has the advantages of being simple and of producing 90–96% pure silymarin (silymarin I–IV) in a yield of approx. 1.7%. Only by employing the selected procedures which are the subject of this invention—namely the use of anhydrous ethyl acetate and a chlorine substituted alkane such as chloroform—is it possible to isolate substantially pure silymarin from the fruits of Silybum marianum.

The effect of the extraction of the drug with anhydrous ethyl acetate is especially inventive compared with the technical status. Hydrophilic materials in the drug remain in the residue. During the following processes, such as distribution in solvents, these hydrophilic accompanying materials cannot normally be completely separated from the silymarin.

Furthermore, the efficiency of distribution of the components in solvent systems methanol/chloroform or methanol/chlorine-substituted lower alkane is especially surprising. The distribution of the components is specifically selective; that is, the methanolic phase contains the active ingredient silymarin almost exclusively, whereas the chloroform phase contains practically all the accompanying materials.

EXAMPLES OF THE EXTRACTION OF SILYMARIN (SILYMARIN I–IV)

EXAMPLE 1

300 kg finely pulverized, cold-pressed milk thistle fruits are mixed with 3000 l anhydrous ethyl acetate and heated to 75° C. At this temperature the mixture is vigorously stirred with an intensive stirrer for one hour. It is then filtered and the crude drug residue is extracted twice more with ethyl acetate, as described.

The combined, clarified ethyl acetate solutions are evaporated to dryness at 50° C. in vacuo at 15 mbar. For the purpose of defatting, the residue is stirred three times with 300 l quantities of light petroleum 60°/70° C. at room temperature for 15 minutes and then freed from solvent by drying in vacuo. The crude product thus obtained is redissolved in four times its volume of methanol. The undissolved solid material is separated by centrifugation, washed twice with half the above mentioned quantity of methanol and finally—as it now contains practically no silymarin—discarded.

The combined methanolic solutions are mixed first with chloroform and then with water in proportions by volume 1:1:1 and transferred to a decanting vessel.

The mixture is then thoroughly stirred for 15 minutes and the phases are allowed to separate. The lower phase (the chloroform phase) is then drawn off and extracted with methanol-water in proportions by volume 1:1:1 for 15 minutes. This extraction is repeated five times in all. The chloroform phase is then discarded.

The combined aqueous-methanolic phases are evaporated in vacuo at 15 mbar at 50° C. and the residue is suspended in five times its volume of methanol. The suspension is then added in a thin stream to ten times its volume of water with continuous stirring, which is then continued vigorously for a further 15 minutes. The mixture is then centrifuged and the solid material is washed by resuspending it in water several times and recentrifuging. The product is dried in a vacuum oven at 40° C. for 24 hours, pulverized and again dried at 40° C. for a further 48 hours.

The result is a light beige powder which has a silymarin content of 90–96% (determined by the dinitrophenylhydrazine method (DNPH method) as used for the determination of silymarin in milk thistle fruits, DAB VIIth edition 1968, $2^{nd}$ supplement 1965, page 198).

Identification is carried out by thin layer chromotography.

The proportions of the individual isomers are determined by quantitative evaluation of the remission curves (see FIG. 1).

The yield amounts to 4.9 kg, equivalent to 1.7% of the crude drug in dry form.

EXAMPLE 2

The same procedure carried out with methylene chloride in place of chloroform gives a product containing 90–96% of silymarin.

The yield amounts to 1.7%.

EXAMPLE 3

The same procedure carried out with 1,2-dichloroethane in place of chloroform gives a product containing 90–93% of silymarin.

The yield amounts to 1.7%.

EXAMPLE 4

The same procedure carried out with trichlorethylene in place of chloroform gives a product containing 90-94% of silymarin.

The yield amounts to 1.8%.

Valid for All Examples

Percentage purity and little variations concerning the yield depend on the drug.

We claim:

1. An improved method for the extraction of silymarin from the fruits of Silybum marianum, the method being the type wherein a large part of the oil is removed from the fruits by cold pressing, the compressed mass is broken up, and the pressed residue extracted to obtain silymarin, the improvement comprising steps of extracting the broken up compressed mass with anhydrous ethyl acetate to remove the silymarin therefrom;

evaporating the ethyl acetate to leave a fatted residue; defatting the residue;

extracting a methanolic solution of the defatted residue with a chlorine-substituted lower alkane, with the addition of water;

extracting the chlorine-substituted solvent with a methanol-water solution;

combining all of the methanolic solutions and evaporating the solvent to leave a product residue;

suspending the product residue in a small amount of methanol; pouring the suspended residue into water;

separating the methanol-water mixture from the material in suspension and drying the material in suspension to yield the desired product.

2. The method of claim 1 wherein the residue is defatted by extraction with a low boiling petroleum solvent.

3. The method of claim 2 wherein the residue is dissolved in methanol before extraction with the petroleum solvent.

4. The method of claim 1 wherein:

the broken up mass is extracted two to four times with anhydrous ethyl acetate at 65° to 76° C. in a 1:8 to 1:12 proportion;

the fatted residue is defatted by extracted with a low boiling petroleum solvent in a 1:15-1:25 ratio of residue to petroleum solvent;

the defatted residue is dissolved in 6-10 times its weight of methanol;

the methanol solution of defatted residue is extracted with chloroform as the chlorine-substituted lower alkane and water each in a volume about equal to that of the methanol solution;

extracting the chloroform with methanol-water is accomplished with a volume ratio of about 1:1:1 of chloroform:methanol:water.

* * * * *